mid et al.

(12) United States Patent
Schmid et al.

(10) Patent No.: US 7,674,477 B1
(45) Date of Patent: Mar. 9, 2010

(54) BONE AND TISSUE SCAFFOLDING FOR DELIVERY OF THERAPEUTIC AGENTS

(75) Inventors: Steven R. Schmid, Lakeville, IN (US); Glen L. Niebur, South Bend, IN (US); Dale R. Sumner, Oak Park, IL (US)

(73) Assignee: University of Notre Dame du Lac, Notre Dame, IN (US)

( * ) Notice: Subject to any disclaimer, the term of this patent is extended or adjusted under 35 U.S.C. 154(b) by 484 days.

(21) Appl. No.: 11/325,530

(22) Filed: Jan. 5, 2006

Related U.S. Application Data (63) Continuation-in-part of application No. 10/980,425, filed on Nov. 4, 2004.

(60) Provisional application No. 60/517,408, filed on Nov. 6, 2003.

(51) Int. Cl.
*A61K 9/22* (2006.01)
*A61F 2/02* (2006.01)

(52) U.S. Cl. ............... 424/422; 424/423; 424/424; 424/425; 424/427; 604/890.1; 604/891.1

(58) Field of Classification Search ............... 424/422, 424/423, 424, 425, 427; 604/890.1, 891.1
See application file for complete search history.

(56) References Cited

U.S. PATENT DOCUMENTS

| 4,011,602 | A |  | 3/1977 | Rybicki et al. |
| 5,750,103 | A |  | 5/1998 | Cherksey et al. |
| 6,440,734 | B1 | * | 8/2002 | Pykett et al. ............... 435/372 |
| 2003/0006534 | A1 | * | 1/2003 | Taboas et al. ............... 264/401 |
| 2003/0171820 | A1 | * | 9/2003 | Wilshaw et al. ............ 623/23.12 |
| 2005/0100578 | A1 |  | 5/2005 | Schmid et al. |

OTHER PUBLICATIONS

Rotter et al., 1998. Cartilage reconstruction in head and neck surgery: Comparison of resorbable polymer scaffolds for tissue engineering of human septal cartilage. Journal of Biomedicine Materials Research, vol. 42, pp. 347-356.*
Sumner, et al. "Locally Delivered rhTGF-β2 Enhanced Bone Ingrowth and Bone Regeneration at Local and Remote Sites of Skeletal Injury" Journal of Orthopaedic Research, 19, (2001), p. 85-94.
Search Report from PCT/US2004/36997 issued May 18, 2005.
Unknown Author, "MacroPore Resorbable Technology: An Overview," Scientific Data Series in Resorbable Fixation, MKT004 Rev. Jun. 2001, pp. 1-8, Distributed by Medtronic Sofamor Danek, 1800 Pyramid Place, Memphis TN 38132, (Jun. 2001).
Holmes et al., "Protected Bone Regeneration," Scientific Data Series in Resorbable Fixation, MKT003 Rev. Jun. 2001, pp. 1-11, Distributed by Medtronic Sofamor Danek, 1800 Pyramid Place, Memphis TN 38132, (Jun. 2001).

* cited by examiner

*Primary Examiner*—Jon P Weber
*Assistant Examiner*—Kailash C Srivastava
(74) *Attorney, Agent, or Firm*—Connolly Bove Lodge & Hutz LLP (57) ABSTRACT

The present invention provides a bone in-growth surface for implants which has a structure for delivering therapeutic agents to surrounding bone and tissue. The bone in-growth surface may comprise scaffolding and a controlled-permeability layer which contains the therapeutic agents in a variety of reservoirs. The porosity of the scaffolding may be controllable from zero porosity to essentially a fully porous material.

40 Claims, 5 Drawing Sheets

BONE AND TISSUE SCAFFOLDING FOR DELIVERY OF THERAPEUTIC AGENTS

CROSS-REFERENCE TO RELATED APPLICATIONS

This application is a continuation-in-part of U.S. application Ser. No. 10/980,425, entitled "Bone and Tissue Scaffolding and Method for Producing Same," filed on Nov. 4, 2004, which claims the priority of U.S. Provisional Patent Application No. 60/517,408, entitled "Bone and Tissue Scaffolding and Method for Producing Same," filed Nov. 6, 2003, the entire contents and disclosure of which are hereby incorporated by reference herein.

BACKGROUND

1. Field of the Invention

The present invention relates generally to local administration of therapeutic agents, and more particularly, to bone and/or tissue scaffolding for delivery of therapeutic agents.

2. Related Art

Implantable medical devices are widely accepted and used in several applications such as microelectronic implants, for example, cardiac implant stimulators, neurostimulators, etc., and musculoskeletal and orthopedic implants, for example, hip, knee, and other joint replacements, etc. Due to improvements in medical implant technologies and the demographics of recipients, these medical implants have been in use are being used for many decades.

Such implants are often made of rigid materials and are in contact with the more flexible surrounding bone and tissue, which over time cause the implant to loosen. Loosening of the implant compromises the ability of the implant to perform its intended function and can be painful to the implant recipient. In situations where loosening occurs, the implant will often have to be replaced. To prevent loosening, several materials have been developed over the years. One type of material, commonly referred to as in-growth scaffolding, is a porous material having an open-celled structure to allow the surrounding bone or soft tissue to advance into the pores, which anchors the implant to the surrounding tissue. In the case of traditional orthopaedic implants, the in-growth material allows osteointegration between the implant and bone.

In addition to loosening, other problems that develop with implants over time include disease, infection, inflammation, etc. While porous in-growth scaffolding material provides a mechanism for integration of the device, such material cannot prevent diseases, inflammations, infections, etc., of the bone and tissue surrounding the implant. One source of such disease, inflammation and infection is from polymer debris shed from the implant and absorbed by the recipient. Also even with scaffolding materials, the surrounding bone tissue may require growth promotion therapies. Further, if there is a need to treat the bone and tissue surrounding the implant with a pharmaceutical or biological agent, conventional scaffolding does not provide the ability to provide such treatment.

SUMMARY

According to one aspect of the present invention, there is provided a bone in-growth surface for delivering a therapeutic agent comprising: in-growth scaffolding; and a controlled-permeability layer having at least one therapeutic agent holding area, wherein said scaffolding at least partially surrounds said controlled-permeability layer. The holding area may contain a therapeutic agent that is released into the bone or tissue surrounding the implant through the porous in-growth scaffold.

According to another aspect of the present invention, there is provided a medical device comprising an implant and a porous in-growth surface. The porous in-growth surface comprises scaffolding and a controlled-permeability layer having at least one therapeutic agent holding area substantially within the controlled-permeability layer. Scaffolding partially surrounds the controlled-permeability layer and the controlled-permeability layer partially surrounds at least part of an implant.

According to a further aspect of the present invention, there is provided a method of delivering a therapeutic agent from a porous in-growth surface comprising: releasing from the therapeutic agent holding area a first therapeutic agent; and diffusing the first therapeutic agent through the controlled-permeability layer and into the scaffolding to provide a therapeutic effect. The in-growth surface comprises scaffolding partially surrounding a controlled-permeability layer having at least one therapeutic agent holding area substantially within thereof, which partially surrounds at least part of an implant.

According to an additional aspect of the invention, there is provided an in-growth surface for delivering a therapeutic agent comprising: growing means for bone or tissue having an open-celled structure; and holding means for a therapeutic agent; and controlling means for diffusing the therapeutic agent from the holding means into the growing means, wherein the growing means partially surrounds an implant and wherein the controlling means and holding means are interposed between the growing means and the implant.

BRIEF DESCRIPTION OF THE DRAWINGS

The invention will be described in conjunction with the accompanying drawings, in which.

DETAILED DESCRIPTION

Embodiments of the present invention provide a bone or soft tissue in-growth surface for an implant or medical device configured to provide a vehicle for delivery of therapeutic agents. Such a delivery vehicle may provide, for example, local administration of therapeutic agents. An in-growth surface as used through out this application generally refers a material which typically surrounds at least part of an implant and that allows "tissue in-growth" and/or "tissue on-growth." For the purposes of the present invention, the term "in-growth" refers to a material's ability to allow or encourage the formation of tissue into and onto a porous scaffolding to achieve an intimate junction having substantially superior fixation. For the purposes of the present invention, the term "on-growth" refers to apposition of tissue on the surface of a material. The porosity of the in-growth surface, in some embodiments, may influence the rate at which bone or tissue may form within the pores of the scaffolding. In addition, the porosity may influence the rate at which therapeutic agents are delivered to the surrounding bone and/or tissue.

A tissue in-growth surface may comprise scaffolding and a controlled-permeability layer having therapeutic agent holding area or reservoirs substantially within said controlled-permeability layer. The controlled-permeability layer is designed with a controlled diffusion rate, which may vary throughout the controlled-permeability layer. The scaffolding partially surrounds the controlled-permeability layer and the controlled-permeability layer partially surrounds at least part of an implant or medical device. The therapeutic agent holding area contains, encapsulates, or is coated or impregnated with one or more therapeutic agents. Embodiments of the present invention may be used with any implant or medical device that is surrounded, partially or fully, by bone or other tissue where integration or fixation of the device to the tissue is desirable. Such implants may include microelectronic, musculoskeletal, orthopedic, spinal, dental, sports medicine, vascular and soft tissue implants.

As used throughout this application, the term "therapeutic agent" refer to any type of drug, medicine, pharmaceutical, hormone, antibiotic, protein, gene, growth factor, bioactive material, etc., used for treating, controlling, or preventing diseases or medical conditions. The therapeutic agent may be suspended, emulsified or dissolved in the holding areas. The therapeutic agent may treat or heal diseases, inflammation, infections, and other maladies, which occur in the body near the implant. Also, therapeutic agents may be used to promote cell differentiation, proliferation, and/or migration. Therapeutic agents may be used to promote tissue formation and/or growth. One example of a therapeutic agent that may be used with embodiments of the present invention is recombinant human transforming growth factor-beta-1 (TGF-$\beta_1$) and transforming growth factor-beta-2 (TGF-$\beta_2$). Recombinant human TGF-$\beta$ has been shown to promote bone growth in scaffolds, as described in Sumner, et al., "Locally delivered rhTGF-$\beta_2$ enhances tissue ingrowth and bone regeneration at local and remote sites of skeletal injury," *J. Orthop. Res., Vol.* 19(1), January 2001, pages 85-94, the entire contents and disclosures of which are hereby incorporated by reference. Other examples of growth factor therapeutic agents include the TGF-beta superfamily (e.g., TGF-$\beta$, bone morphogenic proteins, such as BMP-2, BMP-7, and the like), fibroblast growth factors, vascular endothelial growth factors, insulin-like growth factors, interleukins, transcription factors, matrix metalloproteinases to enhance tissue asperity regeneration, or proteins such as oseopontin, integrins, matrix receptors, RGB and the like, and drugs such as bisphosphbnates (e.g., etidronate, alendronate, risendronate, ibandronate, zolendronate, etc.), hormones such as estrogen, parathyroid hormone (PTH), vitamins/minerals such as calcium, selective estrogen receptor modulators such as raloxifene, human growth hormone, 1,25-(OH)$D_3$ (vitamin $D_3$ and vitamin D), sodium fluoride, etc.

Figure 1:
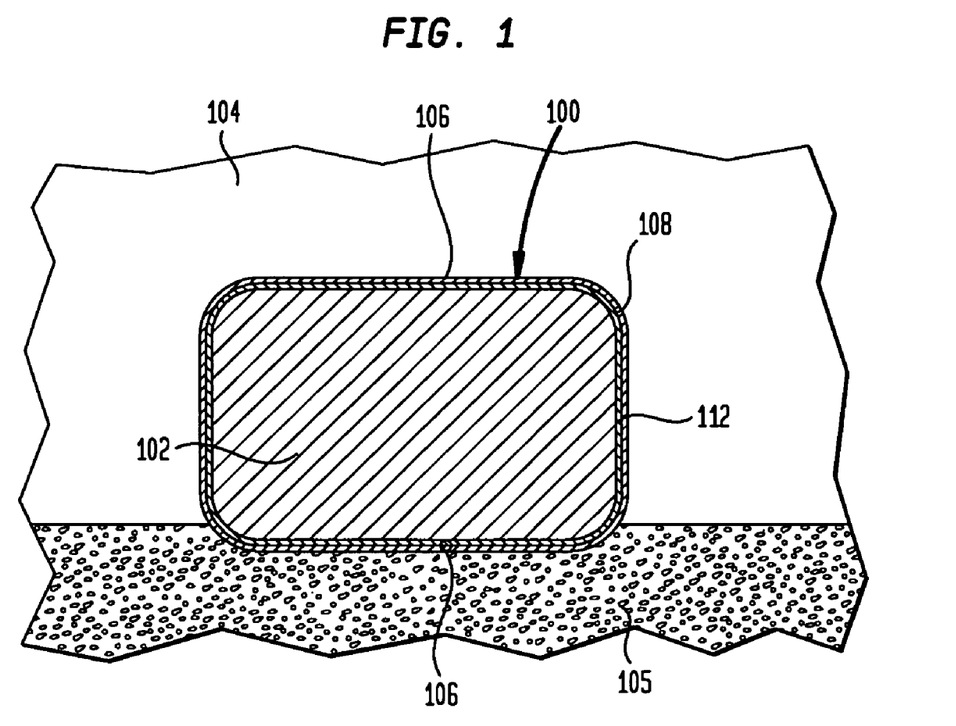
FIG. 1 illustrates a schematic cross-sectional view of a medical device shown implanted in a patient in accordance with an embodiment of the present invention.

FIG. 1 is a schematic representation of a medical device 100 shown implanted in a patient and the surrounding bone 104 and tissue 105. FIG. 1 provides a high-level view of the medical device 100 and its primary elements. For example, FIG. 1 may illustrate a cross-section of the femoral stem of a hip implant that is inserted into the femur and is partially surrounded by the bone or other tissue. Medical device 100 comprises an implant 102 with a bone in-growth surface 106. Surface 106 comprises outer scaffolding 108 and a controlled-permeability layer 112 interposed between implant 102 and scaffolding 108. Scaffolding 108 provides a porous environment in which surrounding bone 104 and/or tissue 105 grows. The openings or voids (not shown) in scaffolding 108 may substantially align with the openings of controlled-permeability layer 112. The interaction of the bone in-growth and on-growth with scaffolding 108 osteointegrates medical device 100 with bone 104.

Controlled-permeability layer 112 is designed having a known diffusion rate for therapeutic agents that are released from one or more reservoirs (not shown) interposed in controlled-permeability layer 112 or between controlled-permeability layer 112 and implant 102. The reservoirs are configured to contain therapeutic agents thereby allowing surface 106 to controllably deliver the agent to the surrounding bone 104 or tissue 105, preferably in a timed-release fashion. Controlled-permeability layer may have a uniform diffusion rate along the coated surface of implant 102. Alternatively, controlled-permeability layer 112 may be partitioned such that there may be different diffusion rates at different locations of the medical device 100. In addition, bone in-growth or on-growth does not occur beyond controlled-permeability layer 112.

Although in FIG. 1, implant 102 is shown partially surrounded by bone 104, implant 102 may also be entirely surrounded by bone 104 or other tissue. Also, although in FIG. 1 surface 106 completely surrounds implant 102, surface 106 may also partially surround implant 102. In such embodiments, surface 106 may be applied to that portion of implant 102 that is adjacent to bone or other tissue 104. Further, although scaffolding 108 is shown completely surrounding controlled-permeability layer 112, scaffolding 108 may partially surround controlled-permeability layer 112. Still further, controlled-permeability layer 112 may also partially surround implant 102. In addition there may be multiple regions on implant 102 which are surrounded surface 106. The extent to which surface 106 surrounds implant 102, scaffolding surrounds controlled-permeability layer 112, and controlled-permeability layer 112 surrounds implant 102 may be determined by the type of implant 102 and the implant location. Embodiments of the present invention may have various surface designs to provide a versatile delivery vehicle for therapeutic agents.

Figure 2A:
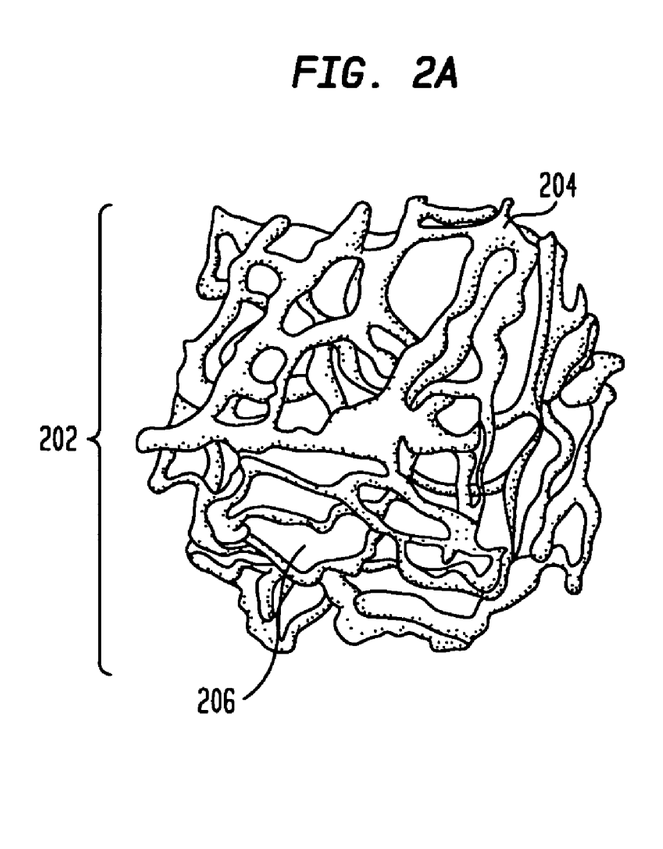
FIG. 2A is a perspective view of scaffolding in accordance with an embodiment of the present invention.
Figure 2B:
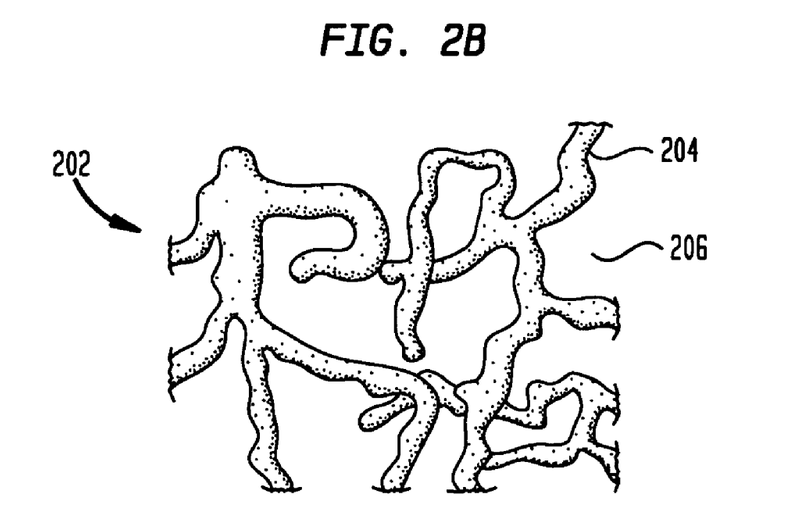
FIG. 2B is a sectional view of the scaffolding of FIG. 2A.

FIGS. 2A and 2B illustrate an open-celled structure of scaffolding 108 described in FIG. 1 in accordance with an embodiment of the present invention. For the purposes of the present invention, the term "open-celled structure" refers to a porous, highly permeable structure in which no significant surface barriers exist between adjacent cells. In particular, an example of a fully open-celled structure is Trabecular Metal™, and an example of a partially open-celled structure is a typical polymer foam.

FIG. 2A is a perspective view of scaffolding 108 and FIG. 2B is a cross-sectional view of the scaffolding illustrated in FIG. 2A. Scaffolding 202 comprises an interlinked network of struts 204 that define an open-celled structure 206 for bone or tissue in-growth. Open-celled structure 206 creates a porous and permeable environment to allow bone and tissue in-growth. In-growth openings 206 and struts 204 are configured to facilitate in-growth, and preferably approximates the trabecular structure of the bone or an optimum geometry for bone in-growth. In one embodiment, struts 204 approximate the diameter of cells in the trabecular bone, which varies in diameter from approximately 0.05 mm to about 2 mm and, preferably, approximately 0.08 mm to 0.3 mm thick. Open-celled structure 206 may be substantially aligned with openings in other layers when scaffolding 202 is used in a bone in-growth surface. In one embodiment, scaffolding 202 is produced using a manufacturing process which allows a prior design of the size, geometry, interconnectivity and branching of struts 204 and open-celled structure 206.

Figure 3A:
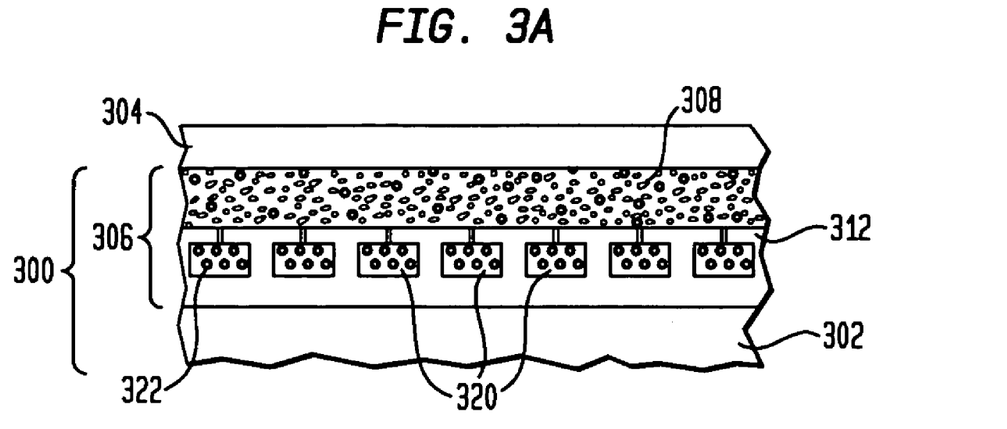
FIG. 3A is a sectional view of a bone in-growth surface having a therapeutic agent filled resorbable polymer beads in accordance with an embodiment of the present invention.

FIG. 3A shows a section of a medical device 300 comprised of an implant 302 with surface 306 adjacent to a bone or other tissue 304 constructed in according to one embodiment of the present invention. Surface 306 comprises scaffolding 308 and a controlled-permeability layer 312 having a therapeutic agent reservoir 320 disposed between controlled-permeability layer 312 and implant 302. Contained within this embodiment of controlled-permeability layer 312 there are a plurality of resorbable polymer volumes 320 that serve as therapeutic agent reservoirs or holding areas, which contain a therapeutic agent 322. Resorbable polymer 320 may comprise any bio-degradable or bio-absorbable polymer, such as polylactic acid (PLA) and polyglycolic acid (PGA). In addition, resorbable polymer 320 may alternatively or alternately comprise autograft or allograft mixed with therapeutic agents. Therapeutic agents 322 may be released by resorbable polymers 320 and diffused through controlled-permeability layer 312 and into scaffolding 308. Therapeutic agents 322 may be absorbed by the recipient through, for example, the surrounding bone 304 or tissue (not shown). Resorbable polymer 320 may be solid, semi-solid, liquid, emulsion, suspension, powder or bead in consistency.

Resorbable polymer 320 may be various sizes, from approximately 1 mm to 5000 mm depending on the bead material, to accommodate different therapeutic agents 322. Polymer sizes can range between 1 and 5000 micrometers, depending on the therapeutic agent and the material. A variety of differently sized or constituted resorbable polymer 320 may be used to delivery one or more therapeutic agents. Also, the same approximately sized resorbable polymer 320 may delivery one or more therapeutic agents. Further, the release rate of the resorbable polymer 320 may be determined by the type of material or type of therapeutic agent contained therewith. These resorbable polymer 320 may be positioned substantially throughout controlled-permeability layer 312 dependant on the type of implant.

Figure 3B:
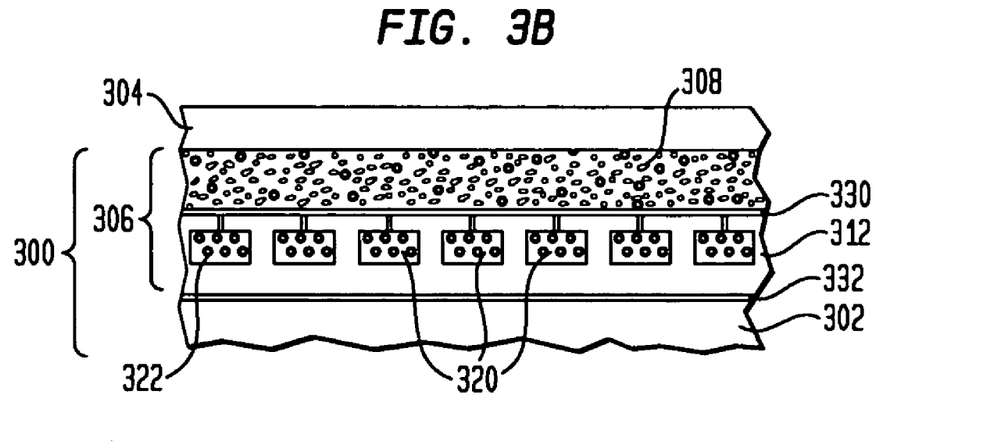
FIG. 3B is a sectional view of the surface of FIG. 3A having additional transitional layers.

FIG. 3B shows a scaffolding transition layer 330 and an implant transition layer 332. Transition layers 330 and 332 may further enhance the structural bond within surface 306 and between surface 306 and implant 302. Transition layers may be bonded to implant 302 or between scaffolding 308 and controlled-permeability layer 312 using adhesive bonding or other suitable bonding means such as friction welding, ultrasonic welding, cold welding, laser welding, resistance welding, arc welding, brazing, glazing, etc.

Figure 4A:
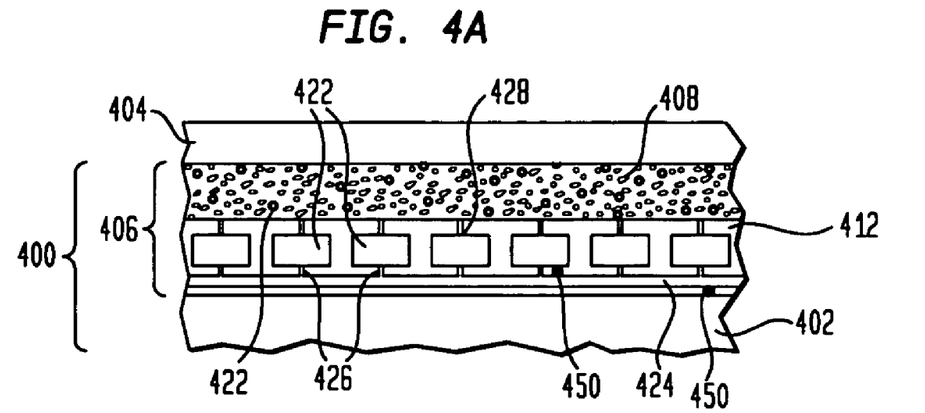
FIG. 4A is a sectional view of a bone in-growth surface having a runner for connecting reservoirs in accordance with an embodiment of the present invention.
Figure 4B:
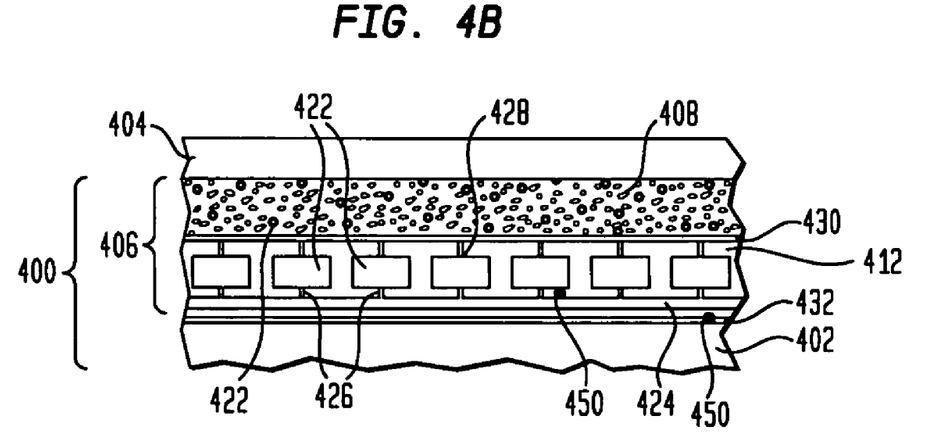
FIG. 4B is a sectional view of the surface of FIG. 4A having additional transitional layers.

FIG. 4A shows a section of a medical device 400 comprised of an implant 402 with a bone or tissue in-growth surface 406 adjacent to a bone or other tissue 404 constructed in accordance with one embodiment of the present invention. Surface 406 comprises scaffolding 408 and a controlled-permeability layer 412. Between controlled-permeability layer 412 and runner system 424 there is a reservoir or a plurality of reservoirs 420. In this embodiment, reservoirs 420 serve as therapeutic agent holding areas or volumes in surface 406. Reservoirs 420 can hold one or more therapeutic agents 422 and, in certain embodiments, may be filled with additional therapeutic agents 422 through a runner 424. Runner 424 is shown as an interconnected runner network having an accessible end (not shown) through which therapeutic agents 422 may be introduced. Each reservoir 420 is fluidically coupled to runner 424 through a gate 426. Therapeutic agents 422 are released from reservoir 420 through output port 428 into controlled-permeability layer 412 and, ultimately, into scaffolding 408. Therapeutic agents 422 may be absorbed by the patient through the surrounding bone 404 or tissue (not shown). FIG. 4B shows a scaffolding transition layer 430 and an implant transition layer 432. Transition layers 430 and 432 may further enhance the structural bond within surface 406 and between surface 406 and implant 402, as discussed above in reference to FIG. 3B. A piezoelectric pumping mechanism with encapsulated power source or pressure vessel can be used to force or aid diffusion across the permeability layer.

A marker may used to identify accessible proximal end (not shown), i.e. port. The radio-lucent marker allows a surgeon or other medical professional to locate the point at which holding areas 420 may be refilled using fluoroscopy or other medical imaging techniques. For example, when conduits 424 are present, radio-lucent marker may identify the proximal end through which therapeutic agents 422 may be introduced using, e.g., a needle or syringe. In some embodiments, fluorescence marker 450 may identify one or more holding areas 420 through which therapeutic agents 422 may be introduced.

Figure 4C:
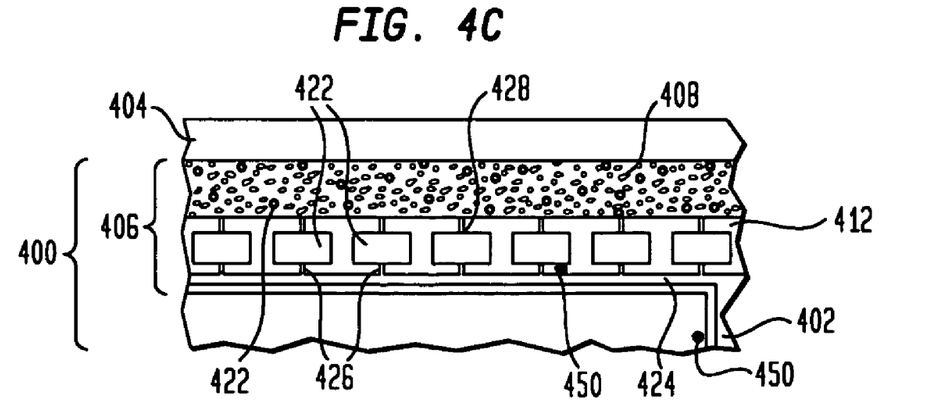
FIG. 4C is a sectional view of the surface of FIG. 4A showing the interconnected runner network extending into the implant.

FIG. 4C shows one embodiment of the present invention in which runners 424 extend into and through implant 402. Although shown extending through implant 402, runners 424 may be located in any manner to allow access from outside the patient without traveling through implant 402. Such arrangements allow the proximal end to be in a more readily accessible location in either the implant or from outside the patient to allow the introduction of therapeutic agents 422. For example, accessible end may be located in the bone and tissue and may be accessible with a needle or syringe. In addition, accessible end may be located along the skin surface which may provide ready access to introduce therapeutic agents.

In some embodiments of the present invention reservoirs may consist of both resorbable polymers bead, as exemplified in FIGS. 3A and 3B, and an interconnected runner network having a plurality of reservoirs, as exemplified in FIGS. 4A-4B. Such arrangement may allow delivery of one or more different types therapeutic agents. Also, such arrangement may allow the refill of a particular type of therapeutic agent in only part of the reservoirs, while the remaining reservoirs continue to release other therapeutic agents. Further, the number of reservoirs that may be included in a surface may vary depending on the type of implant.

Embodiments of the present invention also provide for bone in-growth surfaces for implants that may be obtained by producing a material with three regions: an outer region with bone in-growth porosity and cell shape, a central region with a stiffness that closely matches trabecular bone (roughly 3 GPa elastic modulus), and a solid metal core. This allows the stiffness of the implant to be tailored so that stress shielding of bone does not occur, bone in-growth is optimized, and, as a result, a vigorous and healthy bone may be maintained. Further embodiments of the present invention provide for layered scaffolds serving various purposes. For example, a material of the present invention may have a layer with a finite thickness intended to integrate with tissue, beneath which is a layer designed to contain and control the release of therapeutic agents encapsulated by a bioresorbable material. Beneath this bioresorbable material layer may be a transition to a solid layer suitable for bonding to a solid core, or that comprises the implant core.

Such embodiments of the present invention may provide a superior topography and density for the integration of therapeutic agent, such as bioactive materials. Such an embodiment may take the form of a biologic material that is incorporated directly, such as a bioresorable polymer that contains or encapsulates growth protein, antibiotic, steroid and the like. Such an embodiment may also take the form of a biomaterial or growth factor, antibiotic, steroid and the like that is encapsulated within the material. In this form, a barrier layer may be designed of a resorbable material, or a partial barrier with controlled permeability may be produced to control the release of the biomaterial.

Figure 5:
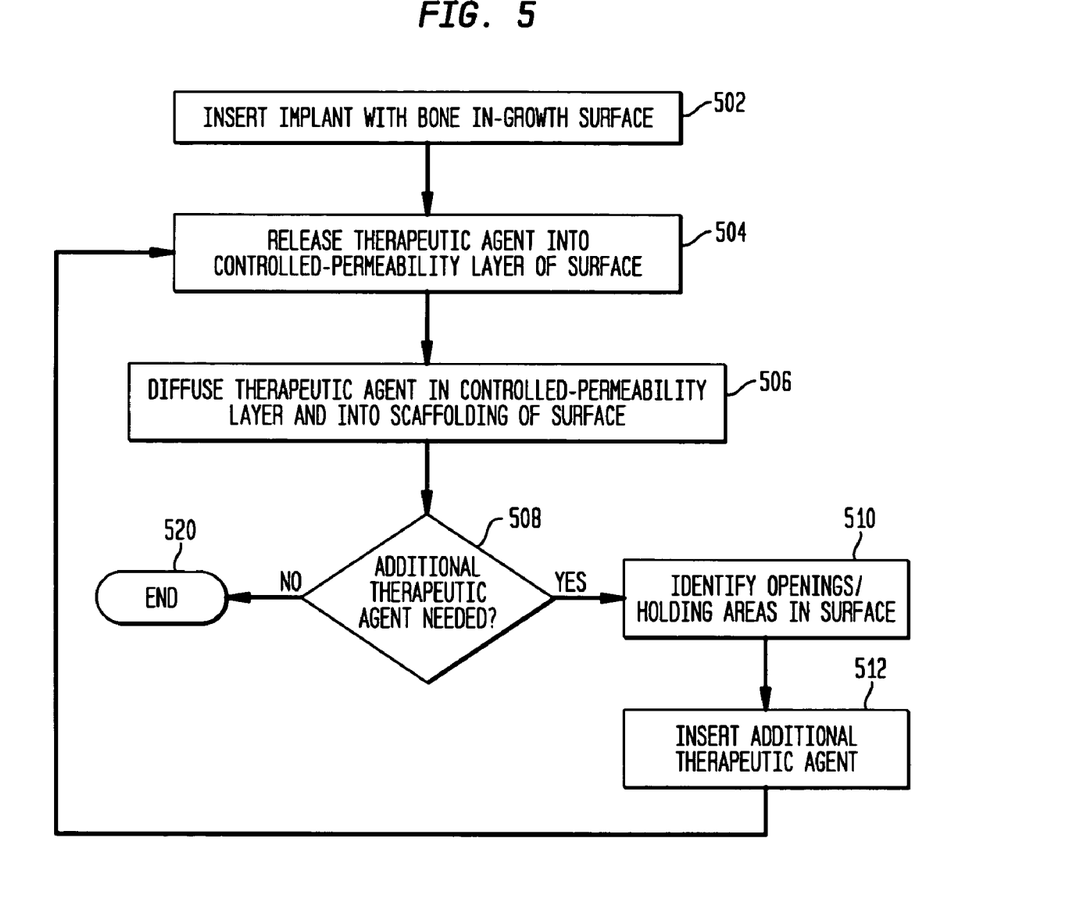
FIG. 5 is a flowchart of the therapeutic delivery process in accordance with an embodiment of the present invention.

FIG. 5 is a flowchart illustrating a method for delivering therapeutic agents in accordance with an embodiment of the present invention. In step 502, the implant having the therapeutic agent bone in-growth surface is inserted to the patient by a surgeon. The surface has holding areas, such as resorbable polymers beads or reservoirs, filled with therapeutic agents. The surface may be arranged according to various embodiments of the present invention and has a controlled-permeability layer and scaffolding. In step 504, the therapeutic agents are released from the holding areas. The approximate release rate is known based on the rate of resorption of the carrier material, i.e. holding areas, (bioresorbable plastic or other pellets) and the controlled-permeability layer used. In some embodiments, it may be desirable to have a variety of release rates for different holding areas or locations on the implant. Once released in step 504, the therapeutic agents are diffused through the controlled-permeability layer in step 506. The approximate diffusion rate is known based on the controlled-permeability layer. Similarly, the diffusion rate may vary for different portions of the controlled-permeability layers to allow flexibility in delivery of the therapeutic agents. Further in step 506, therapeutic agents diffuse out of the controlled-permeability layer into the scaffolding. The controlled-permeability layer may have openings that substantially align with the in-growth openings in the scaffolding. This alignment may further allow the therapeutic agents to easily pass between the controlled-permeability layer and scaffolding. Once in the scaffolding, the therapeutic agents may provide a therapeutic effect.

In step 508, a surgeon or other trained medical professional may decide to add a second therapeutic agent, either a different agent or the same agent in with a different dosage. If the decision is made to add a therapeutic agent, the holding areas are located and identified in step 510. The refilling of therapeutic agent may be done in vivo or ex vivo. The holding areas or the runners connected to the holdings areas may have a marker that are identified in step 510 using fluoroscopy or other imaging techniques. In step 512, the therapeutic agent is inserted using, e.g., a needle or syringe, and the process repeats with step 504. This decision can be made days, weeks, or even years after first implantation.

Assuming the decision is made not to add a therapeutic agent in step 508 the process is terminated at 520. This may occur when resorbable polymer beads are used in the controlled-permeability layer and no therapeutic agent may be added once the beads are absorbed into the patient.

Scaffolding materials, as well as other materials for the controlled permeability layer, transitional layers, reservoirs and runners, etc., are described in co-pending U.S. application Ser. No. 10/980,425, the entire contents and disclosures of which are incorporated by reference. Such materials may include metal beads, metal pads, roughened surfaces, Trabecular Metals™, (HEDROCEL™), porous bioceramics, titanium and titanium alloys, tantalum and tantalum alloys, niobium and niobium alloys, stainless steel, gold and cobalt-chrome alloys, polymer or reinforced polymer, such as nylon, polycarbonate, polymethylmethacrylate, polyethylene, polyurethane, polyaryl etherketone, polyetheretherketone, polylactide, polyglycolide polylactide-co-glycolide and synthetic or natural collagen, bioresorbable thermoplastics, non-bioresorbable thermoplastics, poly(DL-lactide) (DLPLA), poly (L-lactide) (LPLA), poly(glycolide) (PGA), poly(ε-caprolactone) (PCL), poly(dioxanone) (PDO), poly(glyconate), poly (hydroxybutyrate) (PHB), poly(hydroxyvalerate (PHV), poly (orthoesters), poly(carboxylates), poly(propylene fumarate), poly(phosphates), poly(carbonates), poly(anhydrides), poly (iminocarbonates), poly(phosphazenes), and the like, as well as copolymers or blends thereof, polyethylenes, such as high density polyethylene (HDPE), ultra high molecular weight polyethylene (UHMWPE), and low density polyethylene (LDPE), as well as polybutylene, polystyrene, polyurethane, polypropylene, polyaryletherketone, polyacrylates, polymethacrylates, such as polymethylmethacrylate (PMMA), and polymerized monomers such as tri(ethylene glycol) dimethacrylate (TEG-DMA), bisphenol a hydroxypropyl methacrylate (bis-GMA), and other monomers listed herein below, and the like, as well as copolymers or blends thereof and combinations thereof, ceramic, such as alumina, partially stabilized zirconia, hydroxyapatite (HA), piezoelectric materials include quartz, barium titanate, rochelle salt, lead zirconium titanate (PZT), lead niobium oxide, polyvinyl fluoride, etc.

Scaffolding may be produced by a batch manufacturing processes, as well as other manufacturing processes, as described in co-pending U.S. application Ser. No. 10/980, 425, the entire contents and disclosures of which are incorporated by reference. Other manufacturing processes for making scaffolding include layered manufacturing, microstereolithography, chemical vapor deposition, conventional foam-production, direct or indirect production of ceramic scaffolding, direct-write processes such as solid free-form fabrication, extrusion-based robotic deposition (also referred to as "robocasting") and three-dimensional printing (3DP), laser machining, chemical machining or etching, photochemical machining, plasma etching, stamping, electron beam machining and textile manufacturing processes, blow molding, dip coating, solvent casting, spin coating, extrusion, calendaring, injection molding, compression molding, tape casting, doctor blade process, robocasting, jiggering, powder metallurgy approaches of pressing and sintering, cold and hot isostatic pressing, metal injection molding, selective laser sintering, jiggering and sintering, and slip casting, etc. Powder metallurgy approaches may include expansion by agents such as titanium dihydride. Powder metallurgy approaches may include the use of a perform before sintering, and leaching of one or more materials to obtain a porous structure. Ceramic scaffolds using doctor blade process, powder injection molding, cold and hot isostatic pressing, etc. Scaffolding can also be produced by sintering beads, diffusion bonding wires, or plasma spraying particles onto a surface.

In one embodiment of the present invention, scaffolding is created as described in U.S. application Ser. No. 10/980,425, the entire contents and disclosure of which are incorporated by reference, whereby all sheets of a scaffolding are produced, treated as necessary, and then all sheets are joined simultaneously in a batch process, instead of sequentially as in rapid prototyping operations, to form a scaffolding layer. Such a manufacturing approach may involves the following steps:

(a) Sheets of at least one metal, polymer, ceramic or composite are machined, for example, through laser machining, chemical etching, photochemical blanking, electroforming, stamping, plasma etching, ultrasonic machining, water jet cutting, electrical discharge machining or electron beam machining of individual layers, or a porogen that is removed by dissolution, melting, pyrolysis, etc.

(b) Any slag, splatter, maskant or other contaminants that result from laser machining may be removed, for example, through chemical machining or an equivalent process.

(c) The sheets are stacked in a mold produced from graphite or other suitable material to produce the desired product. The graphite or other suitable material preferably has a higher melting temperature than the sheet material and, according to embodiments of the present invention, is preferably chemically inert with respect to the sheet material at elevated temperatures.

(d) The mold is tightened to subject the layers to compressive stress sufficient to compress the layers, but not large enough to cause significant plastic deformation.

(e) The mold is placed in a vacuum furnace, or other heating means, to diffusion bond the sheet layers. The temperatures used in diffusion bonding vary by material, but are roughly 90% of the melting temperature on an absolute temperature scale.

After diffusion bonding, the bone in-growth material or scaffolding is as porous as the layers from which it was constructed. The porosity is controllable from zero porosity to essentially a fully porous material. While bone in-growth materials such as sintered metal wires and beads produce porosities of roughly 20%, the materials according to the processes of the present invention may easily achieve a porosity of from about 5% to about 95%, and may achieve infinitesimally small porosities or porosities approaching 100%. The pore size may be as small as achievable by a machining processes (roughly 10 nanometers for thin foils) and may be very large, for example, hundreds of millimeters in diameter. This process allows for a versatility and control in the material microstructure and porosity that is unmatched by any other known manufacturing process. The scaffolding of embodiments of the present invention is designed and produced through micromachining and may contain any number of layers including those described throughout this application. In such scaffolding, the therapeutic agent delivering features are incorporated into the design at the time of scaffolding manufacture. Scaffolding may be bonded to a controlled permeability layer, reservoirs, runner and gate system, etc., as described above. Variations and alternatives are more fully described in U.S. application Ser. No. 10/980,425.

Scaffolding used in embodiments of the present invention may be joined to an implant, with an interposed controlled permeability layer, using adhesive bonding or other suitable bonding means such as friction welding, ultrasonic welding, cold welding, laser welding, resistance welding, arc welding, brazing, glazing, etc. Such techniques may also be used to join the layers within the bone in-growth surface in some embodiments of the present invention.

According to an embodiment of the present invention, an exothermic phase-change polymer may be incorporated into an implant adjacent to the scaffolding. Such a polymer may create excess thermal energy, and thus, in an embodiment of the present invention, an evacuated or partially evacuated layer may be provided on the scaffolding to provide a protection against thermal damage to bone or other tissue. An evacuated or partially evacuated layer has space in the layer for thermal insulation.

According to an embodiment of the present invention, scaffolding may be constructed in whole or in part of a piezoelectric material. Suitable piezoelectric materials include quartz, barium titanate, rochelle salt, lead zirconium titanate (PZT), lead niobium oxide, polyvinyl fluoride, etc. A piezoelectric material generates a voltage when subjected to mechanical stress, and generates a mechanical stress when subjected to a voltage.

All documents, patents, journal articles and other materials cited in the present application are hereby incorporated by reference. Where the definition of terms departs from the commonly used meaning of the term, applicant intends to utilize the definitions outlined in the application, unless specifically indicated.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

The scheme of providing a reservoir containing a therapeutic treatment with a controlled permeability layer can be used with any scaffolding type, and is not restricted to the form described in U.S. application Ser. No. 10/980,425.

The permeability layer can be incorporated into the scaffold and/or interface between the scaffold and reservoir or reservoirs.

What is claimed is:

1. A surface configured to at least partially surround an implant and to deliver a therapeutic agent, the surface having a finite thickness and comprising:
    a controlled-permeability layer;
    at least one therapeutic agent holding area positioned between said controlled-permeability layer and said implant; and
    an in-growth scaffolding at least partially surrounding said controlled permeability layer configured for at least one of bone and tissue in-growth,
    wherein said controlled-permeability layer and said at least one therapeutic agent holding area cooperate to control when said therapeutic agent is delivered.

2. The surface of claim 1, wherein said at least one therapeutic agent holding area comprises a resorbable polymer containing a therapeutic agent.

3. The surface of claim 1, wherein said at least one therapeutic agent holding area comprises a reservoir.

4. The surface of claim 1, wherein said at least one therapeutic agent holding area comprises a plurality of reservoirs.

5. The surface of claim 4, wherein each of said plurality of reservoirs comprises a first opening and a second opening, wherein said first opening opens into said controlled-permeability layer and said second opening connects to the distal end of at least one runner, and wherein each of said at least one runner has a proximal accessible end.

6. The surface of claim 5, wherein said proximal accessible end has a marker.

7. The surface of claim 5, wherein said at least one runner comprises a plurality of runners, and wherein said plurality of runners are connected via an interconnected runner network, and wherein said interconnected runner network has an accessible end.

8. The surface of claim 7, wherein said accessible end has a marker.

9. The surface of claim 1, wherein said at least one therapeutic agent holding area has a marker.

10. The surface of claim 1, wherein said at least one therapeutic agent holding area is refillable with a therapeutic agent in vivo or ex vivo.

11. The surface of claim 1, further comprising a first transitional layer interposed between said scaffolding and said controlled-permeability layer.

12. The surface of claim 1, further comprising a second transitional layer interposed between said controlled-permeability and said implant.

13. The surface of claim 1, wherein said scaffolding has openings which are substantially aligned with openings in said controlled-permeability layer.

14. The surface of claim 1, wherein said therapeutic agent comprises at least one of a group consisting of a drug, a medicine, a pharmaceutical, a hormone, an antibiotic, a protein, a gene, a growth factor, and a bioactive material.

15. The surface of claim 1, wherein said controlled-permeability layer has a diffusion rate that is uniform throughout the layer.

16. The surface of claim 1, wherein said controlled-permeability layer has a first diffusion rate at a first region of layer and a second diffusion rate at a second region of the layer.

17. The surface of claim 1, wherein said at least one therapeutic holding area has predetermined release rate of the said therapeutic agent.

18. The surface of claim 1, wherein said ingrowth scaffolding comprises a plurality of bonded layers of porous material, each layer having a porosity between approximately 5% and approximately 95%, mean spacing of cells between approximately 0.05 mm and approximately 5 mm, and strut thickness between approximately 0.05 mm and approximately 2 mm, and wherein said porosity of said material is non-uniform across said plurality of layers.

19. The surface of claim 18, wherein each of said layers have a different porosity.

20. The surface of claim 18, wherein at least a region of the scaffolding has a stiffness that closely matches trabecular bone.

21. A medical device comprising:
an implant having a surface configured to at least partially surround said implant and to deliver a therapeutic agent the surface having a finite thickness and: comprising
a controlled-permeability layer;
at least one therapeutic agent holding area positioned between said controlled-permeability layer and said implant; and
an in-growth scaffolding at least partially surrounding said controlled permeability layer configured for at least one of bone and tissue in-growth,
wherein said controlled-permeability layer and said at least one therapeutic agent holding area cooperate to control when said therapeutic agent is delivered.

22. The medical device of claim 21, wherein said at least one therapeutic agent holding area comprises a resorbable polymer bead containing a therapeutic agent.

23. The medical device of claim 21, wherein said at least one therapeutic agent holding area comprises a reservoir.

24. The medical device of claim 21, wherein said at least one therapeutic agent holding area comprises a plurality of reservoirs.

25. The medical device of claim 24, wherein each of said plurality of reservoirs comprises a first opening and a second opening, wherein said first opening opens into said controlled-permeability layer and said second opening connects to the distal end of at least one runner, and wherein each of said at least one runner has a proximal accessible end.

26. The medical device of claim 25, wherein said accessible end has a marker.

27. The medical device of claim 25, wherein said at least one runner extends out of said controlled-permeability layer.

28. The medical device of claim 25, wherein a plurality of said at least one runners are connected via an interconnected runner network, and wherein said interconnected runner network has an accessible end.

29. The medical device of claim 28, wherein said accessible end has a marker.

30. The medical device of claim 28, wherein a portion of said interconnected runner network extends out of said controlled-permeability layer.

31. The medical device of claim 21, wherein said at least one therapeutic agent holding area has a marker.

32. The medical device of claim 21, wherein said at least one therapeutic agent holding is refillable with a therapeutic agent in vivo or ex vivo.

33. The medical device of claim 21, wherein said implant is an orthopedic implant.

34. The medical device of claim 21, wherein said implant contacts soft tissue.

35. The medical device of claim 21, wherein said therapeutic agent comprises at least one of a group consisting of a drug, a medicine, a pharmaceutical, a hormone, an antibiotic, a protein, a gene, a growth factor, and a bioactive material.

36. A method of delivering a therapeutic agent from an implant which has a surface configured to at least partially surround said implant and to deliver a therapeutic agent the surface having a finite thickness and comprising:
a controlled-permeability layer;
at least one therapeutic agent holding area positioned between said controlled-permeability layer and said implant; and
an in-growth scaffolding at least partially surrounding said controlled permeability layer configured for at least one of bone and tissue in-growth, and
wherein said controlled-permeability layer and said at least one therapeutic agent holding area cooperate to control when said therapeutic agent is delivered;
the method comprising:
releasing from said at least one therapeutic agent holding area a first therapeutic agent; and
diffusing said first therapeutic agent through said controlled-permeability layer and into said scaffolding to provide a therapeutic effect.

37. The method of claim 36, further comprising refilling said at least one therapeutic agent holding area with a second therapeutic agent.

38. The method of claim 37, further comprising locating said at least one therapeutic agent holding area.

39. The method of claim 37, wherein said first and second therapeutic agents are the same.

40. The method of claim 37, wherein said therapeutic agent comprises at least one of a group consisting of a drug, a medicine, a pharmaceutical, a hormone, an antibiotic, a protein, a gene, a growth factor, and a bioactive material.

* * * * *